United States Patent
Liu et al.

(10) Patent No.: US 12,076,360 B2
(45) Date of Patent: *Sep. 3, 2024

(54) HERBAL COMPOSITION PHY906 AND ITS USE IN CHEMOTHERAPY

(71) Applicant: YALE UNIVERSITY, New Haven, CT (US)

(72) Inventors: Shwu-Huey Liu, Madison, CT (US); Zaoli Jiang, Woodbridge, CT (US); Yung-Chi Cheng, Woodbridge, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/236,081

(22) Filed: Aug. 21, 2023

(65) Prior Publication Data

US 2024/0075092 A1 Mar. 7, 2024

Related U.S. Application Data

(63) Continuation of application No. 17/714,530, filed on Apr. 6, 2022, now Pat. No. 11,771,731, which is a continuation of application No. 16/848,233, filed on Apr. 14, 2020, now Pat. No. 11,324,793, which is a continuation of application No. 16/049,381, filed on Jul. 30, 2018, now Pat. No. 10,646,530, which is a continuation of application No. 14/581,610, filed on Dec. 23, 2014, now Pat. No. 10,058,580, which is a continuation of application No. 13/648,597, filed on Oct. 10, 2012, now abandoned, which is a continuation-in-part of application No. 12/527,302, filed as application No. PCT/US2008/053965 on Feb. 14, 2008, now Pat. No. 8,309,141.

(60) Provisional application No. 60/901,310, filed on Feb. 15, 2007.

(51) Int. Cl.
| | | |
|---|---|---|
| A61K 36/00 | (2006.01) | |
| A61K 31/4412 | (2006.01) | |
| A61K 31/7068 | (2006.01) | |
| A61K 36/484 | (2006.01) | |
| A61K 36/539 | (2006.01) | |
| A61K 36/65 | (2006.01) | |
| A61K 36/725 | (2006.01) | |

(52) U.S. Cl.
CPC ........ *A61K 36/725* (2013.01); *A61K 31/4412* (2013.01); *A61K 31/7068* (2013.01); *A61K 36/484* (2013.01); *A61K 36/539* (2013.01); *A61K 36/65* (2013.01)

(58) Field of Classification Search
CPC .... A61K 36/65; A61K 36/725; A61K 36/484; A61K 36/539
See application file for complete search history.

(56) References Cited

U.S. PATENT DOCUMENTS

| | | |
|---|---|---|
| 4,613,591 A | 9/1986 | Aburada et al. |
| 5,414,015 A | 5/1995 | Konoshima et al. |
| 5,437,866 A | 8/1995 | Sun |
| 5,552,440 A | 9/1996 | Crooks et al. |
| 5,595,756 A | 1/1997 | Bally et al. |
| 5,665,393 A | 9/1997 | Chen et al. |
| 6,048,847 A | 4/2000 | Ramadoss et al. |
| 6,630,176 B2 | 10/2003 | Li et al. |
| 7,025,993 B2 | 4/2006 | Cheng et al. |
| 7,534,455 B2 | 5/2009 | Cheng et al. |
| 8,309,141 B2 | 11/2012 | Liu et al. |
| 2003/0111180 A1 | 6/2003 | Nagahata et al. |
| 2003/0157126 A1 | 8/2003 | Li et al. |
| 2003/0211180 A1* | 11/2003 | Cheng ............... A61P 31/18 514/49 |
| 2005/0196473 A1 | 9/2005 | Cheng et al. |
| 2011/0111070 A1 | 5/2011 | Cheng et al. |
| 2013/0101688 A1 | 4/2013 | Liu et al. |
| 2015/0182575 A1 | 7/2015 | Cheng et al. |

FOREIGN PATENT DOCUMENTS

| | | |
|---|---|---|
| CN | 1271590 A | 11/2000 |
| EP | 0943620 A2 | 9/1999 |
| JP | 7118161 A | 5/1995 |
| WO | WO0166123 | 9/2001 |
| WO | WO2006053049 | 5/2006 |
| WO | WO2008101079 | 8/2008 |
| WO | 2009055769 A1 | 4/2009 |

(Continued)

OTHER PUBLICATIONS

Jacobs, A. D. Gemcitabine-Based Therapy in Pancreas Cancer: Gemcitabine-Docetaxel and Other Novel Combinations. Cancer Supplement, 95: 923-927, 2002.
McGinn, C. J., Lawrence, T. S., and Zalupski, M. M. On the Development of Gemcitabine-Based Chemoradiotherapy Regimens in Pancreatic Cancer. Cancer Supplement, 95: 933-940, 2002.
Oettle, H. and Riess, H. Gemcitabine in Combination with 5-Fluorouracil with or without Folinic Acid in the Treatment of Pancreatic Cancer. Cancer Supplement, 95: 912-922, 2002.
Gelmon, K., Chan, A., and Harbeck, N. The role of capecitabine in first-line treatment for patients with metastatic breast cancer. The Oncologist. 11( suppl I): 42-51, 2006.

(Continued)

*Primary Examiner* — Qiuwen Mi
(74) *Attorney, Agent, or Firm* — Henry D. Coleman; R. Neil Sudol

(57) ABSTRACT

This invention provides herbal compositions useful for increasing the therapeutic index of chemotherapeutic compounds. This invention also provides methods useful for improving the quality of life of an individual undergoing chemotherapy. Furthermore, this invention improves the treatment of disease by increasing the therapeutic index of chemotherapy drugs by administering the herbal composition PHY906 to a mammal undergoing such chemotherapy.

20 Claims, 6 Drawing Sheets

(56) References Cited

FOREIGN PATENT DOCUMENTS

WO    2009152228    12/2009

OTHER PUBLICATIONS

Ershler, W. B. Capecitabine monotherapy: safe and effective treatment for metastatic breast cancer. The Oncologist. 11(4):325-35, 2006.
Martin, M. J. Current stage-specific chemotherapeutic options in colon cancer. Expert Rev Anticancer Ther. 5(4):695-704, 2005.
Cartwright, T. H., Cohn, A., Varkey, J. A., et al. A Phase IIstudy of oral capecitabine in patients with advanced or metastatic pancreatic cancer. J Clin Oncol. 20: 160-164, 2002.
Lozano, R. D., Patt, Y. Z., Hassan, M. M., Frome, A., Vauthey, J. N., Ellis, L. M., Schnirer, T. D., Brown, J. L., Abbruzzese, J. L., Wolff, R. A., and Chamsangavej, C. Oral Capecitabine (Xeloda) for the treatment of hepatobiliary cancers (hepatocellular carcinoma, cholangiocarcinoma, and gallbladder cancer). Proc Am Soc Clin Oncol. 19:1025A, 2000.
Stromberg, D., Richly, H., Hilger, R.A., et al. Phase I clinical and pharmacokinetic study of the novel Raf kinase and vascular endothelial growth factor receptor inhibitor BAY 43-9006 in patients with advanced refractory solid tumors. J Clin Oncol. 23: 965-972, 2005.
ACS Cancer Facts and Figures. American Cancer Society, 2004.
Raymond, E., Faivre, S., Chaney, S., Woynarowski, J., and Cvitkovic, E. Cellular and Molecular Pharmacology of Oxaliplatin. Molecular Cancer Therapeutics, 1: 227-235, 2002.
Diggle, P. J., Liang, K. Y., and Zeger, S. L. Analysis of Longitudinal Data, 2nd ed. Oxford: Oxford Science Publications, 1994.
Macphillamy, H.B.; Plant Science Bulletin, Apr. 1963; vol. 9, issue 2, pp. 1-15.
Raskin et al.; Can an Apple a Day Keep the Doctor Away?; Current Pharmaceutical Design, 2004, vol. 10, pp. 3419-3429.
Liu SH, et al. Prevention of CPT-11 Induced Toxicity by a Chinese Medicinal Formulation, PHY-906. Proceedings of the American Association for Cancer Research Annual, 2000;41:410 XP001018859.
Liu SH, et al. A Chinese Medicine Formulation, PHY-906, Can Enhance the Therapeutic Index of CPT-11 and other Anticancer Drugs Against Cancer in Mice. Proceedings of the American Association for Cancer Research Annual, 2001;42:85 XP001018879.
Narita M, et al. Inhibition of Beta-Glucuronidase by Natural Glucurondes of Kampo Medicines Using Glucuronide of SN-38(7-Ethyl-10-Hydroxycamptothecin) as a Substrate. Xenobiota, 1993;23(1):5-10.
Takasuna, et al. Protective Effects of Kampo Medicines and Baicalin Against Intestinal Toxicity of a New Anticancer Camptothecin Derivative, Irinotecan Hydrochloride (EPT-11), in Rats. Japanese Journal of Cancer Research, 1995;86(10):978-984.
Mori K, et al. Kampo medicines for the Prevention of Irinotecan-Induced Diarrhea in Advanced Non-Small cell Lung Cancer. Gan T. Kagaku Ryoho Japanese Journal of Cancer and Chemotherapy, 1998;25(8):1159-1163.
Goldberg RM, et al. Irinotecan Plus 5-Fu and Leucovorin in Advanced Colorectal Cancer: North American Trails. Oncology, 1998;6 Suppl 6;59-63.
Bleiberg H, et al. European J of Cancer, 1999;35(3):371-379.
Stucky-Marshall L. Cancer Nursing, 1999;22(3):212.
Suzuki, et al. Suppressor Macrophages: A Role on the Growth of Transplanted Tumors and Regulation by an Extract of Licorice, Glycyrrhizin. Oncologia (Tokyo), 1987;20(5):124-133.
Govindarajan, et al. Lancet, 2000;356:566.
Liu SH, et al. Developing PHY-906 as a Broad-Spectrum Modulator of Chemotherapeutic Agents in Cancer Therapy. Proceedings of the Annual Meeting of the American Association for Cancer Research, 2004;45:128.
Nagai, et al. Antiviral Activity of PLant Flavonoid, 5,7,3'-Trihydrozy-8-methoxyflavone, from the Roots of Scutellaria baicalensis against Influenza A (H3N2) and B Viruses. Biol Pharm Bull, 1995;18(2):295-299.
Huang L, et al. Zhonggou Zhong Yao Za Zhi, 1990;15(2):115-117, 128.
Smol'ianinov ES, et al. Eksp Klin Farmakol, 1997;60(6):49-51.
Hande, et al. Metabolism and Excretion of Etoposide in Isolated, Perfused Rat Liver Models. Cancer Res, 1998;46(20):5692-5695.
Sommadossi, et al. Modulation of 5-Fluorouracil Catabolismin Isolated Rat Hepatocytes with Enhancement of 5-Fluorouracil Glucoronide Formation. Cancer Res, 1985;45(1):116-121.
Certain Chinese Herbal Medicine Prescriptions, 1979.
Yogatrangini by Trimalla Bhatta—Commentary by Duttarama Mathura; Chaukhamba Vidyabhavan, Varanasi, Edn Reprint 2003, p. 169; FID: RG/4478 Form name: Badarikalkah.
Bogar 700 by Bogar, Ed. Ramachandran, Pub: Thamaral Noolagam Chennai (1994), p. 8-13, FID: PD03/02; Form name: Maha Mega Rasangam.
Li R, et al. Evaluation of Clinical Efficacy and Review on Progress of Antineoplastic Drugs. Evaluation and Analysis of Drug-use in Hospital of China, 2004;4(1).
Li D. Progress on Clinical Application of Thalidomide. Chinese Journal of Clinical Pharmacy, 2004;13(2).
Saif MW, et al. Phase I study of the botanical formulation PHY906 with capecitabine in advanced pancreatic and other gastrointestinal malignancies. Phytomedicine, 2010.
Yen Y, et al. Phase I/II Study of PHY906/Capecitabine in Advanced Hepatocellular Carcinoma, Anticancer Research, 2009:29:4083-4092.
Farrell, et al. Phase I/IIA Randomized Study of PH906, a Novel Herbal Agent, as a Modulator of Chemotherapy in Patients with Advanced Colorectal Cancer. Clinical Colorectal Cancer, 2003;2(4):253-256.
Liu, et al. R&D and Clinical Trial of HPY906 in the USA. GP-TCM Congress, Leiden, Netherlands, 2012.
Kummar, et al. Phase I Study of the Chinese Herbal Medicine PHY906 as a Modulator of Irinotecan-based Chemotherapy in Patients with Advanced Colorectal Cancer. Clinical Colorectal Cancer, 2011;10(2):85-96.
Lam, et al. The Four-Herb Chinese Medicine PHY906 Reduces Chemotherapy-Induced Gastrointestinal Toxicity. Sci Transl Med, 2010;2:45-59.
Alsamaral, et al. A phase I study of PHY906 as a modulator of Irinotecan (CPT-11) in patients with advanced solid tumors. J of Clinical Oncology, 2010;28(15):E13571.
Saif, et al. Phase II study of PHY906 plus capecitabine (CAP) in patients with gemcitabine-refractory pancreatic cancer (PC) and measurement of cytokines. J of Clinical Oncology, 2010;28:abstract e14540.
Wang, et al. Interaction of a traditional Chinese Medicine (PHY906_ and CPT-11 on the inflammatory process in the tumor microenvironment. BMC Medical Genomics, 2011;4:38.
Saif, et al. A Phase II study of capecitabine (CAP) plugs PHY906 in patients (pts) with advanced pancreatic cancer. J of Clinical Oncology, 2010;27:abstract e15508.
Saif, et al. Is there a Role for Herbal Medicine in the Treatment of Pancreatic Cancer? J. Pancrease, 2008;9(4):403-407.
Liu, et al. Old formula, new Rx: The Journey of PHY906 as a cancer adjuvant therapy. Journal of Ethnopharmacology, 2012;140:614-623.
Tilton, et al. A comprehensive platform for quality control of botanical drugs (PhytomicsQc): a case study of Huangqin Tang (HQT) and PHY906. Chinese Medicine, 2010;5:30.
Liu, et al. Evidence-based Anticancer Material Medica for Pancreatic Cancer, Materia Medica for Various Cancers, 2010: Chapter 11.
Liu, et al. Controlling Chemotherapy-Related Side Effects with Chinese Medicine. Supportive Cancer Care with Chinese Medicine, 2012; Chapter 7.
Liu, et al. PHY906 in hepatocellular carcinoma. Proceedings of the American Association for Cancer Research, Annual Meeting 2007;48:439.
Liu, et al. Botanical activity relationship in traditional Chinese medicine: Studies of PHY906 as an adjuvant therapy with cancer chemotherapeutic agents. Proceedings of the American Association for Cancer Research, 2002;43:961.

(56) References Cited

OTHER PUBLICATIONS

Liu, et al. PHY906 as a broad-spectrum enhancer in cancer therapy: Clinical and preclinical results in hepatocellular carcinoma. Proceedings of the American Association for Cancer Research, 2006;47:506.
Lam, et al. Exploration of the mechanism of PHY906 in reducing the intestinal toxicity caused by irinotecan. Proceedings of the American Association for Cancer Research, 2009;50:1106 Annual Meeting.
Grove, et al. Anticancer Activity of B-I-Dioxolane-cytidine, a Novel Nucleoside Analogue with the Unnatural I Configuration. Cancer Res, 1995;55:3008-3011.
Bienvenu JA, Monneret G, Gutowski MC. et al. Cytokine assays in human sera and tissues Toxicology 129: 55-61 (1998).
Bleiherg, H.: CPT-11 in Gastrointestinal Cancer. European Journal of Cancer, vol. 35, No. 3, 371-379, 1999.
Bleiberg, H., Cvitkovic, E.:Characterization and clinical management of CPT-11 (irinotecan)-induced adverse events: The European perspective. Eur. J. Cancer 32A(Suppl 3):S18-S23, 1996.
Calabresi P. and Chabner BA: Chemotherapy of Neoplastic Diseases, Goodman & Oilman's the Pharmocological Basis of Therapeutics, Ninth Edition, Section X:1225-1232, 1996.
Chen J. J.W. Wu R, Yang PC, et al. Profiling expression patterns and isolating differentially expressed genes by cDNA microarray system with colorimetry detection. Genomics 51:313-324 (1998).
Chu, X-Y, Kato, Y, Ueda, K. et al. Biliary Excretion Mechanism of CPT-11 and Its Metabolites in Humans: Involvement of Primary Active Transporters. Cancer Res. 58:5137-5143, 1998.
Douillard J., Cunningham D., Roth A., Germa J., J.ames R., Karasek P., Jandik P., Iveson T., Cannichael J., Gruia G., Dembak M., Slbaud D., Rougier P.: A randomized phase m trial comparing Irinotecan + 5FU/Follnic Acid (FA) to the same schedule of SFU/FA in patients (pts) with metastatic colorectal cancer (MCRC) as front line chemotherapy {CT}, Proc. ASCO, vol. 18, 233a, 1999.
Gilman, M. 1993. Ribonuclease protection assay. In Current Protocols in Molecular Biology, vol. 1.(Ausubel, F.M., R. Brent, R.E. Kingston, D.D. Moore, J.G. Seidman, J.A. Smith and K. Stuhl, eds.), pp. 4.7.1-4.7.8, John Wiley and Sons, Inc., New York.
Guo X, Lerner-Tung M, Chen HX, Chang CN, Zhu JL, Chang CP, Pizzomo G, Lin, TS, Cheng YC. 5-Fluoro-2 pyrimidinone, A liver aldehyde oxidase-activated prodrug of 5-fluorouracil. Biochem Pharm, 49, 1111-1116 (1995).
Gupta E, Mick R, Ramirez J, Wang X, Lestingi TM, Vokes EE, Ratain MJ: Pharmacokinetic and phannacodynamic evaluation of the topoisomerase inhibitor irinotecan in cancer patients. J Clio Oncol 15:1502-1510, 1997.
Haaz M.C., Rivory, L., Riche, C., et al. Metabolism of irinotecan (CPT-11)by human hepatic microsomes: participation of cytochrome P-450 3A and drug interactions. Cancer Res 58:468-472 (1998).
Hani Oka Hiroshi, Taki No Ko Sul<e: Application of 212 formula of Kampo Medicine. K.abusiki Kaishya, Tokyo, Japan, 1998.
Joulia, J., Pinguet, F., Ychou, M., Duffour, J., Astre, C. and Bressolle, F.:Plasma and Salivary Phannacokinetics of 5-Fluorouracil (FU) in Patients with Metastatic Colorectal Cancer Receiving FU Bolus Plus Continuous Infusion with High-dose Folinic Acid. European Journal of Cancer, vol. 35, No. 2, 26-301, 1999.
Kaneda N., Nagata H., Furuta T., Yokokura T.: Metabolism and pharmacokinetics of the camptothecin analogue CPT-11 in the mouse. Cancer Res SO: I7151720, I 990.
Kivisto K.T.,Kroemer H.K. and Eichelbaum M. The role of human cytochrome P4S0 enzymes in the metabolism of anticancer agents: implications for drug interactions. Br J. Clio Phannacol 40:523-530 (1995).
Koima K., et. al. Long-term administration of Asho-salkoto@increase cytochrome P-450 mRNA level in mouse liver. Biol. Pharm. Bull. 21:426-428, 1998.
Lombardi V.R.M, Garcia M and Cacabelos L.R.R. Characterization of cytokine production, screening of lymphocyte subset patterns and in vitro apoptosis in healthy and -Alzheimer's Disease (AD) individuals. Journal of Neuroimmunol 97:163-171(1999).

Miller CL and Eaves CJ. Expansion in vitro of adult murine hematopoietic stem cells with transplantable lympho-myeloid reconstituting ability. Proc. Natl. Acad. Sci. 94:13648-13653 (1997).
Mori K., Hirose T., Machida S., Tominaga K.: Kampo medicines for the prevention of irinotecan-induced diarrhea in advanced non-small cell lung cancer. Gan To Kagaku Ryoho 25:1159-63, 1998.
Marita M., Nagai E., Hagiwara H., Aburada M., Yokoi T., Kamataki T.: Inhibition of beta-glucuronidase by natural glucuronides of kampo medicines using glucuronide of SN-38 (7-ethyl-10-hydroxycamptothecin) as a substrate. Xenobiotica 23:5-10, 1993.
Peters, G. and van Groeninger, C.: Clinical relevance of biochemical modulation of 5-fluorouracil. Annals of Oncology 2: 469-480, 1991.
Pinedo, H. and Peters, G.. Fluorouracil: Biochemistry and Pharmacology. Journal of Clinical Oncology, vol. 6, No. 10 (October), 1633-1664, 1988.
Pizzomo G., Wiegand R., Lentz S. and Handschumacher R., Brequinar Potentiates 5-Fluorouracil antitumor activity in a Murine model colon 38 tumor by tissue-specific modulation of uridine nucleotide pools. Cancer Res ., 52: 1660-1665, 1992.
Saliba F, Hagipantelli R, Misset J-L, Bastian G, vassal G, Bonnay M, Herait P, Cote C, Mahjoubi M, Mignard D, Cvitkovic E: Pathophysiology and therapy inirinotecan-induced delayed-onset diarrhea in patients with advanced colorectal cancer: A prospective assessment. J Clin Oncol 16:2745-2751, 1998.
Saltz LB, Locker PK, Pirotta N, Elfring GL, Miller LL: Weekly Irinotecan (CPT-11) , Leucovorin (LV), and Fluorouracil (FU) is superior to dally x5 LV/FU in patients (PTS) with previously untreated metastatic colorectal cancer (CRC), Proc. ASCO, vol. 18, 233a, 1999.
Stucky-Marshall, L.:New Agents in Gastrointestinal Malignancies: Part 1:Irinotecan in Clinical Practice, Cancer Nursing, 22(3): 212-219, 1999.
Takasuna K, Takehiro H, Hirohashi M, Kato M, et al. Involvement of b-glucuronidase in intestinal microflora in the intestinal toxicity of the antitumor camptothecin derivative irinotecan hydrochloride (CPT-11) in rats. Cancer Res. 56:3752-3757 (1996).
Takasuna K, Takehiro H, Hirohashi M, et al. Inhibition of intestinal microflora 0-glucuronidase modifies the distribl fition of the active metabolite of the antitumor agent, irinotecan hydrochloride (CPT-11) in rats. Cancer Chemother Pharmacol. 42:280-286 (1998).
Wasserman E., Myara A., Lokiec F., Goldwasser F., Trivin F., Mahjoubi M., Misset J., Cvitkovic E.: Severe CPT-11 toxicity in patients with Gilbert's syndrome: Two case reports. Ann Oncol 8:1049-1051, 1997.
Wierda D. and Matamoros M. Partial characterization of bone marrow hemopoiesis in mice after cisplatin administration. Toxicol & Applied Phannacol 75:25-34(1984).
Xu Guo-Jun, Introduction to the Chinese Materia Medica, China Pharmaceutical Science Publication Inc., Beijin, China, 1996, p. 398.
Bergsland, E. K. and Venook, A. P. Hepatocellular Carcinoma [Gastrointestinal Tract]. Current Opinion in Oncology, 12: 357-361, 2000.
Fernandez-Zapico, M. E., Kaczynski, J. A., and Urrutia, R. Pancreatic Cancer Research: Challenges, Opportunities, and Recent Developments. Curr Opin Gastroenterol, 18: 563-567, 2002.
Jemal, A., Thomas, A., Murray, T., and Thun, M. Cancer Statistics, 2002. CA Cancer J Clin, 52: 23-47, 2002.
Skolnick, A. A. Basic Science Focus of Third International Symposium on Liver Cancer and Hepatitis. The Journal of the American Medical Association, 276: 1457-1458, 1996.
Abbruzzese, J. L.New Applications of Gemcitabine and Future Directions in the Management of Pancreatic Cancer. Cancer Supplement, 95: 941-945, 2002.
Hertel, L. W., Boder, G. B., Kroin, J. S., Rinzel, S. M., Poore, G. A., Todd, G. C., and Grindey, G. B. Evaluation of the Antitumor Activity of Gemcitabine (2',2'-Difluro-2'-deoxycytidine). Cancer Res., 50: 4417-4422, 1990.
Pettersson, F., Colston, K. W., and Dalgleish, A. G. Retinoic Acid Enhances the Cytotoxic Effects of Gemcitabine and Cisplatin in Pancreatic Adenocarcinoma Cells. Pancreas, 23: 273-279, 2001.

(56) References Cited

OTHER PUBLICATIONS

Philip, P. A. Gemcitabine and PLatinum Combinations in Pancreatic Cancer. Cancer Supplement, 95: 908-911, 2002.

Schultz, R. M., Meriiman, R. L., Toth, J. E., Zimmermann, J. E., Hertel, L. W., Andis, S. L., Dudley, D. E., Rutherford, P. G., Tanzer, D. R., and Grindey, G. B. Evaluation of New Anticancer Agents against the MIA paCa-2 and PANC-1 Human Pancreatic Carcinoma Xenografts. Oncology Research, 5: 223-228, 1993.

Von Hoff, D. D. and Bearss, D. New drugs for patients with pancreatic cancer. Current Opinion in Oncology, 14: 621-627, 2002.

Bruns, C. J., Harbison, M. T., Davis, D. W., Portera, C. A., Tsan, R., McConkey, D. J., Evans, D. B., Abbruzzese, J. L., Hicklin, D. J., and Radinsky, R. Epidermal Growth Factor Receptor Blockade with C225 Plus Gemcitabine Results in Regression of Human Pancreatic Carcinoma Growing Orthotopically in Nude Mice by Antiangiogenic Mechanisms. Clinical Cancer Research, 6: 1936-1948, 2000.

\* cited by examiner

HERBAL COMPOSITION PHY906 AND ITS USE IN CHEMOTHERAPY

CROSS-REFERENCE TO RELATED APPLICATIONS

This application is a continuation application of U.S. application Ser. No. 17/714,530 filed on Apr. 6, 2022, which is a continuation of U.S. application Ser. No. 16/848,233 filed on Apr. 14, 2020, now U.S. Pat. No. 11,324,793 which issued May 10, 2022, which is itself a continuation of U.S. application Ser. No. 16/049,381 filed on Jul. 30, 2018 now U.S. Pat. No. 10,646,530 which issued May 12, 2020, which is itself a continuation application of U.S. application Ser. No. 14/581,610 filed on Dec. 23, 2014, now U.S. Pat. No. 10,058,580 which issued on Aug. 28, 2018, which is itself a continuation application of U.S. patent application Ser. No. 13/648,597 filed on Oct. 10, 2012, which is itself a continuation application of U.S. patent application Ser. No. 12/527,302 filed on Jan. 29, 2010, now U.S. Pat. No. 8,309,141 which issued on Nov. 13, 2012, which is itself a United States national phase patent application of International Patent Application No. PCT/US2008/053965 filed Feb. 14, 2008, which claims priority from provisional application No. 60/901,310 filed Feb. 15, 2007, the contents of which applications are herein incorporated by reference in their entirety for all purposes.

FIELD OF THE INVENTION

The present invention relates to herbal compositions and the use of them for enhancing the therapeutic effects of chemotherapeutic compounds.

BACKGROUND OF THE INVENTION

Cancer remains one of the major cause of death around the world. Specifically, cancer is the second overall cause of death in the United States. Gastrointestinal cancers, including colorectal, liver, and pancreatic cancers, are of particular concerns not only because of their high incidence rates, but also because of their high mortality rate, especially in pancreatic and liver cancer patients (1-4). From years 1992-1999, studies revealed that the five-year relative survival rate of colorectal cancer was 62.3% while that of liver cancer was 6.9% and 4.4% for pancreatic cancer. The median survival of liver cancer was 3.5 weeks to 6 months while it was 4 to 6 months for pancreatic cancer (3). With only very poor chemotherapeutic regimens available, pancreatic cancer has the highest mortality rate among all cancers in the United States, with a less than 5% survival rate 5 years from diagnosis (3). Although several regimens are currently used in clinical trials for hepatocellular carcinoma, there is no FDA-approved chemotherapeutic agent available. The low survival rates for both pancreatic and hepatocellular cancers are attributed to many factors including diagnosis is difficult, the tumor growth is highly aggressive, surgical removal of tumor is of low probability, and the tumor has a high rate of chemotherapy resistance.

SUMMARY OF THE INVENTION

Figure 1:
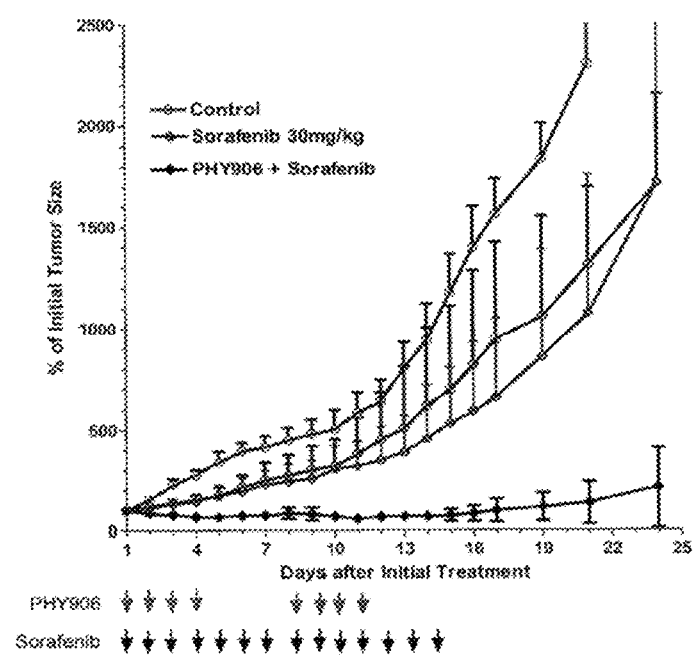
FIG. 1 shows the effect of PHY906 (500 mg/kg, bid. D1-4 and 8-11) on tumor growth in Sorafenib (30 mg/kg, po, bid, D1-14)-treated BDF-1 mouse bearing mouse colon 38 tumors. Sorafenib (30 mg/kg) was given orally twice a day for a consecutive 14 days. PHY906 (500 mg/kg) was given orally 30 min before sorafenib twice a day on days 1-4 and days 8-11 (N=5 in each group).

In one aspect, the present invention provides a composition comprising: i) a pharmaceutically acceptable carrier; ii) an herbal preparation comprising *Scutellaria, Glycyrrhiza, Ziziphus*, and *Paeonia*; and iii) one or more chemotherapeutic compounds.

In another aspect, the present invention provides a method of treating a disease in a mammal in need thereof comprising administering a therapeutically effective amount of a composition comprising: i) a pharmaceutically acceptable carrier; ii) an herbal preparation comprising *Scutellaria, Glycyrrhiza, Ziziphus*, and *Paeonia*; and iii) one or more chemotherapeutic compounds.

In another aspect, the present invention provides a method of increasing the therapeutic index of cancer therapeutic compounds for the treatment of cancer by administering to a mammal in need thereof, a therapeutically effective amount of a composition comprising a pharmaceutically acceptable carrier, and an herbal preparation comprising *Scutellaria, Glycyrrhiza, Ziziphus*, and *Paeonia*.

In yet another aspect, the present invention provides a method of relieving side effects of a chemotherapeutic compound in a mammal comprising administering a composition comprising: i) a pharmaceutically acceptable carrier; ii) an herbal preparation comprising *Scutellaria, Glycyrrhiza, Ziziphus*, and *Paeonia*; and iii) one or more chemotherapeutic compounds.

In yet another aspect, the present invention provides a method of improving the quality of life of a mammal undergoing chemotherapy which comprises administering a therapeutically effective amount of one or more chemotherapeutic compounds and a composition comprising: i) a pharmaceutically acceptable carrier; ii) an herbal preparation comprising *Scutellaria, Glycyrrhiza, Ziziphus*, and *Paeonia*; and iii) one or more chemotherapeutic compounds.

DETAILED DESCRIPTION OF THE INVENTION

Gemcitabine is the only clinically approved chemotherapeutic agent for pancreatic cancer; however, the response rate in patients to gemcitabine is only 6-11% and the overall survival time is generally 4-6 months. Gemcitabine is a nucleoside analog with two mechanisms of action, including the inhibition of ribonucleotide reductase, an enzyme that converts nucleotide diphosphate to deoxynucleotide triphosphate and that is required for DNA synthesis and that competes with deoxycytidine triphosphate as a fraudulent base in DNA synthesis (3,5-10). With the low response and survival rates of gemcitabine monotherapy, several gemcitabine-combination drug regimens have been tested clinically for improving therapeutic efficacy. These trials include gemcitabine with other commonly used and FDA-approved anti-cancer drugs including CPT-11, capecitabine, and oxaliplatin (11-14). Unfortunately, no satisfactory combination drug regimens have been discovered and an effective regimen for pancreatic cancer is urgently needed.

Capecitabine (Xeloda), an oral fluoropyrimidine, is a rationally designed oral prodrug efficiently absorbed from the gastrointestinal tract and converted to 5-FU, preferentially in neoplastic tissues. It has been approved by the FDA as a first-line chemotherapy for the treatment of colorectal and breast cancers with reduced toxicities (15-17). Capecitabine has also shown promising antitumor activity as a single agent in pancreatic cancer (18) and liver cancer (19).

Hepatocellular carcinoma (HCC) is currently treated by surgical procedures and chemotherapy. Surgical removal and postoperative therapies may improve the outlook for some patients. Unfortunately, the vast majority of patients with hepatocellular carcinoma will have unresectable cancers. In late 2007, sorafenib became the first FDA-approved chemotherapeutic agent for HCC. Published clinical studies indicate significant anti-tumor effects (20,21). Oral multikinase inhibitor sorafenib (BAY 43-9006) has a dual-action on Raf kinase and vascular endothelial growth factor. Sorafenib prevents tumor growth by combining inhibition in tumor cell proliferation and tumor angiogenesis. Preclinical studies suggest that sorafenib may offer therapeutic benefits in HCC by blocking Raf-1 signal transduction pathway.

Colorectal cancer has been reported to be the third most common cause of death from cancer in the United States (22). Recently, the FDA approved the triple combination use of Oxaliplatin/5-FU/LV as the first-line treatment for patients with advanced colorectal cancer. Oxaliplatin is a synthesized diaminocyclohexane platinum compound, which like cisplatin, causes platinum-DNA adduct formation and destroys the integrity of DNA (23). Other types of chemotherapeutic agents, such as 5-FU, CPT-11, are common chemotherapeutic agents used in the treatment of colorectal cancer. Unfortunately, severe diarrhea has been identified as one of the dose-limiting toxicities among patients, treated with chemotherapy.

Our studies showed that PHY906, an herbal composition, not only reduced chemotherapy-induced toxicities, including body weight loss and mortality, but it also enhanced the antitumor efficacy of a broad-spectrum of anticancer agents including, but not limited to CPT-11, 5-FU, CPT-11/5-FU/LV, VP-16, L-OddC and oxaliplatin/5-FU/LV in colorectal cancer; sorafenib, capecitabine, thalidomide, and CPT-11 in liver cancer; and capecitabine, oxaliplatin, gemcitabine and gemcitabine/oxaliplatin in pancreatic cancer in vivo animal models. The positive results from these preclinical studies demonstrate that PHY906 can be used as an adjuvant for a broad-spectrum of different types of chemotherapeutic agents in anti-cancer therapy. These chemotherapeutic agents include, but are not limit to, capecitabine and sorafenib. The cancers include, but are not limited to, colorectal, liver, and pancreatic cancers. The methods of the present invention can be used to improve the quality of life of patients including mammals under chemotherapy. Specifically, this invention relates to the dosing and scheduling of PHY906 in potentiating the therapeutic index of a broad-spectrum of cancer chemotherapeutic agents by the herbal composition PHY906.

In one embodiment, the present invention provides a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment, the plant species comprise *Scutellaria baicalensis, Glycyrrhiza uralensis, Ziziphus jujuba*, and *Paeonia lactiflora*. In another embodiment of the invention one or more chemotherapeutic compounds are cancer chemotherapeutics. In one embodiment of the invention the cancer chemotherapeutics are selected from the group consisting of capecitabine, sorafenib, and a combination thereof.

In one embodiment of the invention, a therapeutically effective amount of a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is used to treat a disease in a mammal in need thereof. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment, the present invention provides a method of treating a disease in a mammal. The method comprises administering to the mammal in need thereof a therapeutically effective amount of a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment, the present invention provides a method of relieving the side effects of a chemotherapeutic compound in a mammal. The method comprises administering to the mammal in need thereof a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds.

In one embodiment of the invention, a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is administered to a mammal to enhance the therapeutic effectiveness of chemotherapeutic compound. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment of the invention, a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is administered to a mammal to enhance the antitumor activity of a chemotherapeutic compound. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment of the invention, a therapeutically effective amount of a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is administered to a mammal to treat tumors. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment of the invention, a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is administered to a mammal to inhibit the growth of tumors in mammals. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*.

In one embodiment of the invention, a composition comprising a pharmaceutically acceptable carrier, materials or chemicals from a plant species of each of the following genera of herbs: *Scutellaria, Glycyrrhiza, Ziziphus* and *Paeonia*, and one or more chemotherapeutic compounds is used to inhibit the growth of tumors. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*. In one embodiment, the tumors are present in a mammal or in vitro cells.

In one embodiment, the present invention provides a method of improving the quality of life of a mammal undergoing chemotherapy. The method comprises administering a therapeutically effective amount of one or more chemotherapeutic compounds and a composition comprising: i) a pharmaceutically acceptable carrier; ii) materials or chemicals from a plant species of each of the following genera of herbs: *Scutellaria, Glycyrrhiza, Ziziphus* and *Paeonia*; and iii) one or more chemotherapeutic compounds. In another embodiment, the materials or chemicals from a plant species is in a form of a herbal composition comprising *Scutellaria, Glycyrrhiza, Ziziphus* and *Paeonia*. In yet another embodiment, the herbal composition consists essentially of *Scutellaria, Glycyrrhiza, Ziziphus* and *Paeonia*. Preferably, the mammal as referenced herein is a human.

The above-referenced chemotherapeutic agents or compounds, genera of herbs, and other terms and phrases have been described and defined with details in the following patent applications and patent: U.S. patent application Ser. No. 09/522,055 filed Mar. 9, 2000: International Application No. PCT/US2001/007353 filed Mar. 8, 2001; U.S. patent application Ser. No. 10/220,876 filed Dec. 30, 2002 and issued as U.S. Pat. No. 7,025,993 on Apr. 11, 2006; U.S. Provisional Patent Application Ser. No. 60/625,943 filed Nov. 9, 2004; U.S. patent application Ser. No. 11/100,433 filed Apr. 7, 2005; and International Application No. PCT/US2005/040605 filed Nov. 9, 2005, the content of which are herein incorporated by reference in their entirety for all purposes.

EXAMPLES

Materials and Methods

Drug: Sorafenib (Nexavar) was purchased from Bayer HealthCare (Leverkusen, Germany). Capecitabine (Xeloda®, CAP) was purchased from Roche Laboratories Inc. (Nutley, New Jersey). The clinical drug substance of PHY906 (PHY906-6, FDA 165542) with 10% excipient was prepared by Sun Ten Pharmaceutical, Inc. (Taipei, Taiwan). The PHY906 formula is composed of four herbs: *Scutellaria baicalensis* Georgi, *Paeonia lactiflora* Pall., *Ziziphus jujuba* Mill and *Glycyrrhiza uralensis* Fisch., with a relative weight ratio of 3:2:2:2.

Mice: Female BDF-1 mice with body weights between 16 and 20 g (4-6 weeks old) were purchased from Charles River Laboratories (Wilmington, MA). Male NCr athymic nude mice with body weights between 16 and 20 g (4-6 weeks old) were purchased from Taconic Farms (Germantown, NY).

Preparation of Sorafenib solution: Sorafenib (200 mg/tablet) was dissolved in 5% gum arabic as the vehicle. The final solution contains 30 mg/ml of sorafenib.

Preparation of capecitabine solution from capecitabine tablet: Capecitabine (150 mg/tablet) was dissolved in 40 mM citrate buffer (pH 6.0) containing 5% gum arabic as the vehicle. The final solution contains 36 mg/ml of capecitabine.

Preparation of herbal extract from dry powder: The preparation of the herbal extract followed SOP #HERB-001-PHY906. Briefly, one gram of PHY906 dry powder, containing 10% starch excipient, was added to 10 ml of 80° C. $H_2O$ and incubated at 80° C. for 30 minutes. The supernatant was separated from the debris by centrifugation (12000 rpm, 10 min) at room temperature. The concentration of PHY906 supernatant was calculated as 90 mg/ml of PHY906 (1 g/10 ml×0.9), based on the dry weight of the dry powder. The herbal extract was stored at room temperature and used within 24 hours. Any residual precipitant that occurred upon standing was vortexed into a suspension and used to treat the animals.

Tumor cells: The human hepatocellular carcinoma HepG2, human PANC-1 pancreatic cancer, and mouse Colon 38 colorectal cancer cell lines were purchased from the American Type Culture Collection (Rockville, MD). The HcpG2 and Colon 38 cell lines were routinely grown in MEME media while the PANC-1 cell line was grown in DMEM media, supplemented with 10% fetal bovine serum (FBS). The cells were implanted into the left flank of mice. Tumor transplantation from mice to mice was performed when the tumor reached 1500-2000 mm$^3$.

Mouse tumor model: Tumor cells ($5 \times 10^6$ cells in 0.1 ml PBS) were transplanted subcutaneously into the left flank of mice. After 14 days, tumor ranging in size from 300-500 mm$^3$ was selected for drug studies. The length and width of the each tumor was measured with sliding calipers. The tumor size was estimated according to the following formula:

Tumor size (mm$^3$)=length (mm)×width (mm)$^2$/2.

The studies were conducted and the animals were maintained at the Yale Animal Facility.

Antitumor activity of chemotherapeutic agents in the presence or absence of PHY906: A total of 20 tumor-bearing mice were divided into 4 groups (N=5 mice/group):
1. Vehicle
2. PHY906
3. Chemotherapeutic agent
4. PHY906+Chemotherapeutic agent The first day of drug treatment was defined as day 1. PHY906 (500 mg/kg, bid) was administrated orally to the mice 30 min before chemotherapeutic agents at the days indicated. Chemotherapeutic agents were given either intraperitoneally or orally at the dose and schedule indicated. The tumor size, body weight, and mortality of the mice were monitored daily. Mice were sacrificed when the tumor size reached 10% of body weight.

Immunohistochemistry: Formalin-fixed paraffin-embedded liver tissue was freshly cut into slices of 4 mm. The sections were mounted on Superfrost slides, dewaxed with xylene, and gradually hydrated. Antigen retrieval was achieved by 0.05% citraconic anhydride buffer (pH 7.4) at 94° C. for 1 h. The primary HIF-1α, CD31 or VEGF antibodies was diluted 1:75 using Tris-HCl buffer containing 1% BSA and 0.5% Tween-20. The primary antibody was incubated at room temperature for 1 hour. As a negative control, two slides were processed without primary antibody. Detection took place by the conventional labeled streptavidin-biotin method with alkaline phosphatase as the reporting enzyme according to the manufacturer's instructions. DAB (3,3'-diaminobenzidine tetrahydrochloride, purchased from Sigma-Aldrich. St Louis, MO) served as chromogen. Afterwards, the slides were briefly counterstained with hematoxylin and aqueously mounted.

Statistical analysis and statistical power of the study (24): A random effects model was employed to analyze data from similar dosing animal trials. The PROC MIXED procedure in SAS was used to take into account the correlation among observations collected from the same mouse.

The following model was used to analyze the longitudinal data:

$$y_{ijk} = \mu + \alpha t_k + \beta(I_D t_k) + \gamma(I_P t_k) + \delta(I_D I_P t_k) + e_{ijk},$$

where $y_{ijk}$ is the relative tumor size of the jth individual with the ith group (no treatment, drug alone. PHY900 alone, and drug+PHY906) at the kth time point, $t_k$ is the kth time point, $\alpha$ is the baseline time effect (no treatment group), $I_D$ and $I_P$ are indicator variables for having the drug treatment and the PHY906 treatment, $\beta$ is the drug-specific linear time effect, $\gamma$ is the PHY906-specific linear time effect, $\delta$ is the drug-PHY906 synergistic linear time effect, and $e_{ijk}$ is the residual (error) term. We assumed that the errors from different individuals are independent, and errors from the same individual at different time points follow the autoregressive model. AR (1), to take into account the fact the observations from the same individual within the same treatment group are more correlated, and the responses from closer time points are more correlated within the same individual. The PROC MIXED in SAS 8.01 was used to perform the statistical analysis.

Results (1) Sorafenib
Effect of PHY906 in Antitumor Activity of Sorafenib in Murine Colon 38 Bearing BDF-1 Mice To determine whether the combinational use of PHY906 and sorafenib in order to improve anti-tumor activity of sorafenib. Sorafenib at dose of 30 mg/kg (BID, D1-14), in combination with a fixed dose of PHY906 at 500 mg/kg (BID, D1-4 and 8-11), were studied in BDF-1 mice bearing Colon 38 murine colorectal cancer. As shown in FIG. 1, PHY906 significantly enhanced the antitumor activity of sorafenib in Colon 38 bearing mice. Indeed, the tumor growth was suppressed when mice received the combination of PHY906 and sorafenib.

Figure 2:
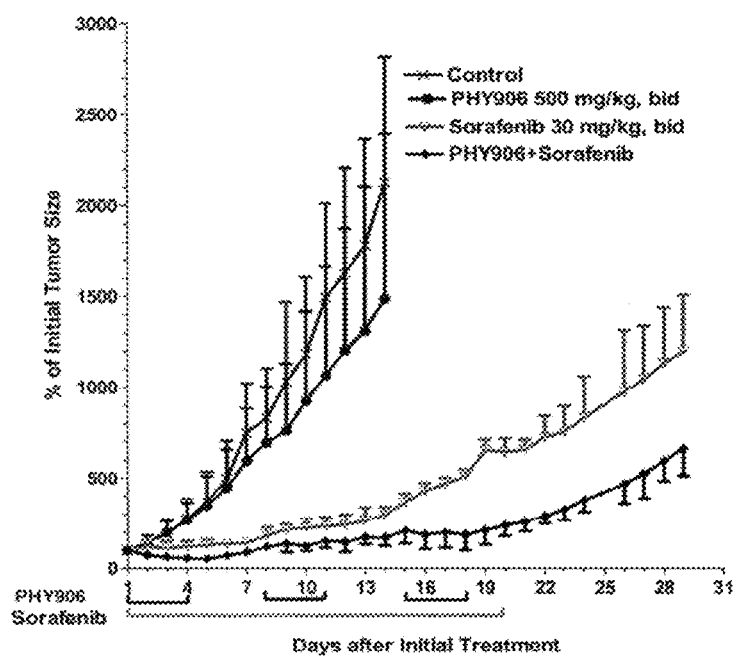
FIG. 2 shows the effect of PHY906 (500 mg/kg, bid. D1-4, 8-11 and 15-18) on tumor growth in Sorafenib (30 mg/kg, po, bid, D1-20)-treated nude mice bearing human HepG2 tumors. Sorafenib (30 mg/kg) was given orally twice a day for a consecutive 20 days. PHY906 (500 mg/kg) was given orally 30 min before sorafenib twice a day on days 1-4, 8-11 and 15-18 (N=5 in each group).

Effect of PHY906 in (a) Antitumor Activity, (b) Blood Vessels, (c) VEGF Level and (d) HIP-1α of Sorafenib in Human HepG2 Xenografts PHY906 (500 mg/kg, BID. D1-4, 8-11 and 15-18) was tested on the antitumor activity of sorafenib (30 mg/kg, BID. D1-20) in human HepG2 bearing nude mice. As shown in FIG. 2, the combination of sorafenib and PHY906 shrank the tumor size approximately 60% after the first week of combination drug treatment while mice treated with sorafenib alone did not have the shrinkage in tumor.

Figure 3:
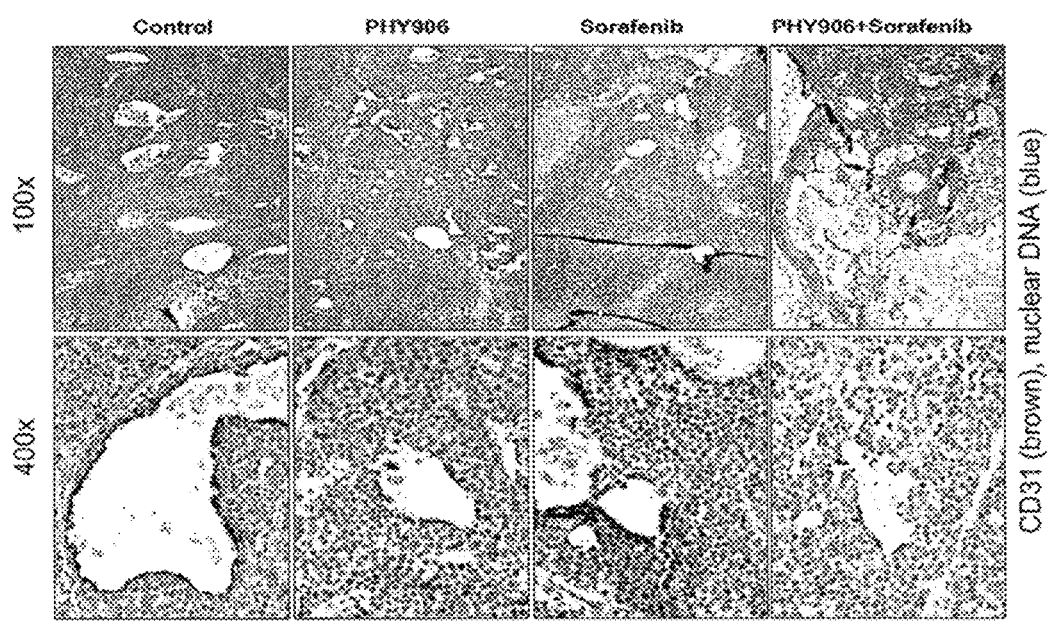
FIG. 3 shows the impact of PHY906 and Sorafenib on blood vessels from the liver of NCr-nude mice bearing human HepG2 xenografts. Tissue sections were prepared from formalin-fixed, paraffin-embedded liver cancer specimens. Immunohistochemical staining was done using specific antibodies against CD31 (brown) and nuclear DNA (blue).
Figure 4:
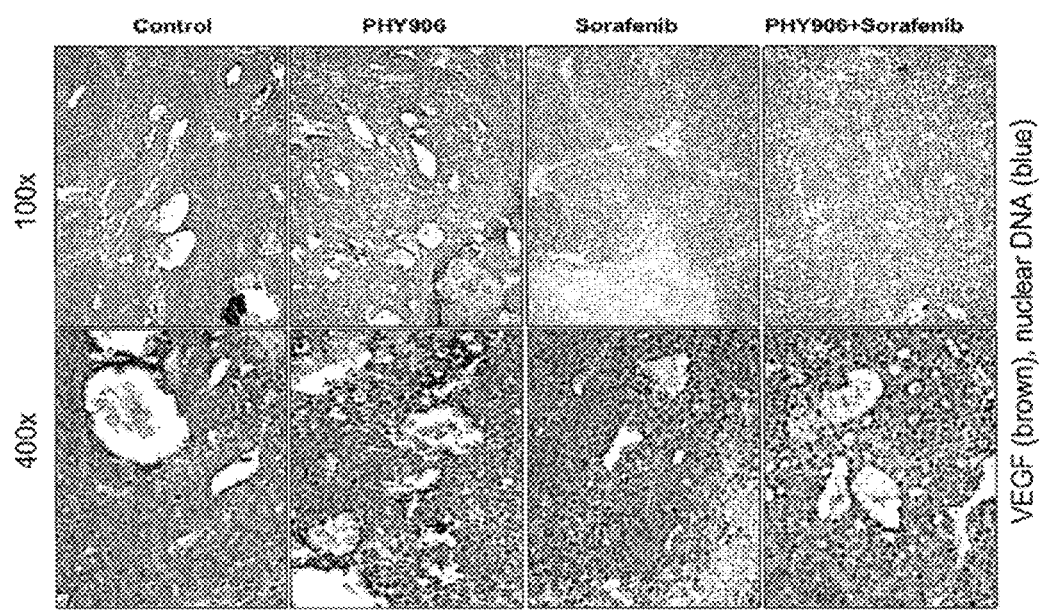
FIG. 4 shows impact of PHY906 and Sorafenib on VEGF level from the liver of NCr-nude mice bearing human HepG2 xenografts. Tissue sections were prepared from formalin-fixed, paraffin-embedded liver cancer specimens. Immunohistochemical staining was done using specific antibodies against VEGF (brown) and nuclear DNA (blue)
Figure 5:
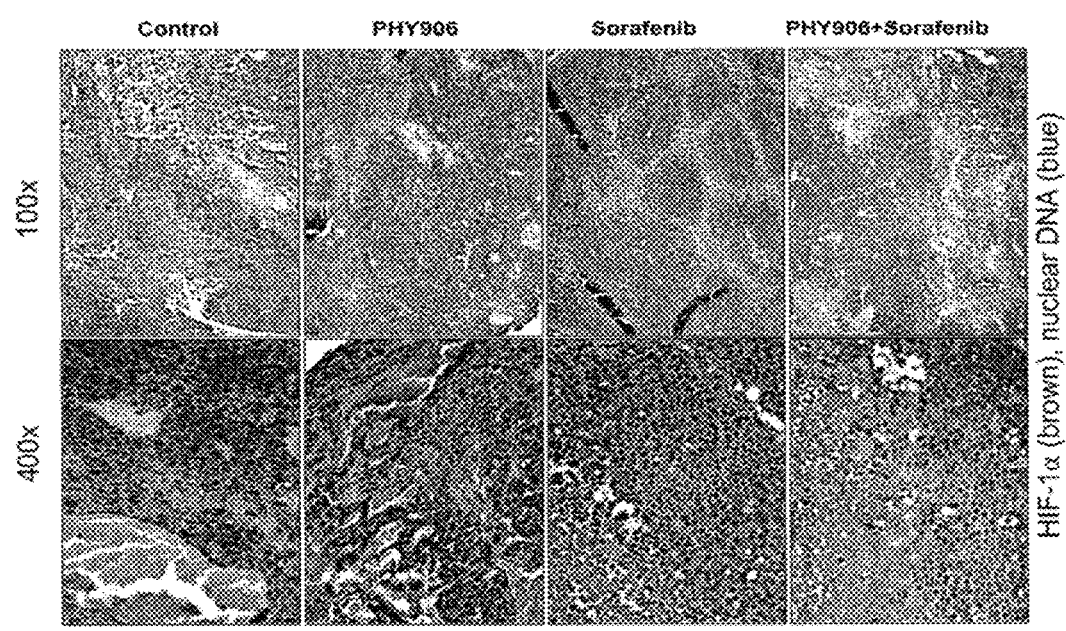
FIG. 5 shows the impact of PHY906 and Sorafenib on HIF-1α level from the liver of NCr-nude mice bearing human HepG2 xenografts. Tissue sections were prepared from formalin-fixed, paraffin-embedded liver cancer specimens. Immunohistochemical staining was done using specific antibodies against HIF-1α (brown) and nuclear DNA (blue).

The immunohistochemical stainings on mouse liver indicate that the integrity of tumor blood vessels are destroyed with the combination treatment of PHY906 and sorafenib, as shown in FIG. 3. The expressions of VEGF and HIF-1α are suppressed by the combination treatment of PHY906 and sorafenib, as shown in FIGS. 4 and 5, respectively. The data also suggests that the combination treatment of PHY906 and sorafenib affects the Fos/Juk transcription.

Figure 6:
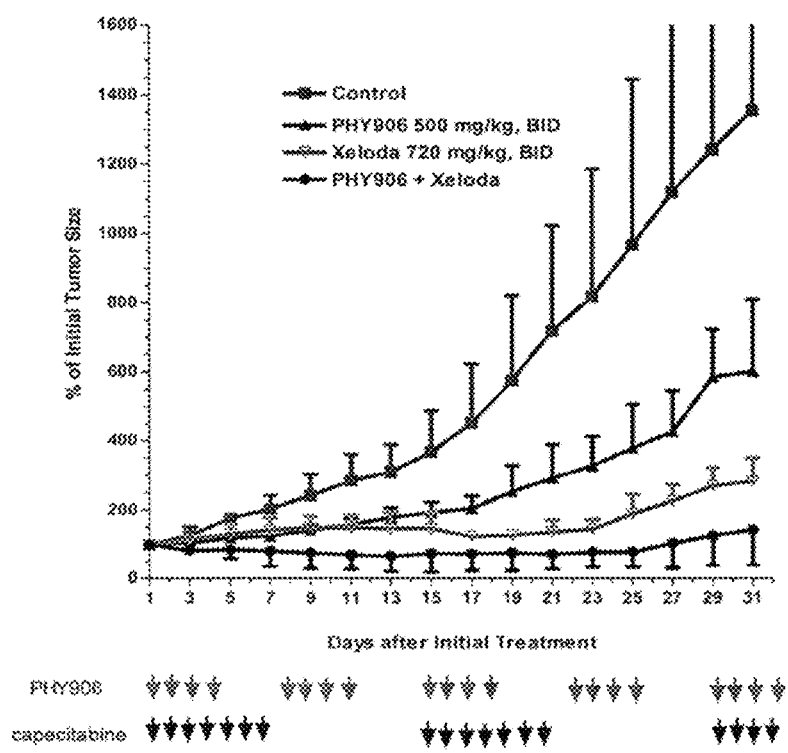
FIG. 6 shows the effect of PHY906 on the tumor growth in Capecitabine-treated NCr-nude mice bearing human Panc-1 tumor. Capecitabine (720 mg/kg) was given orally twice a day on days 1-7, 15-21 and 29-32 days. PHY906 was given orally 30 min before capecitabine twice a day on days 1-4, 8-11, 15-18, 22-25 and 29-32 at 500 mg/kg (N=5 in each group)

(2) Capecitabine
Effect of PHY906 on the Antitumor Activity of Capecitabine in Human Panc-1 Tumor-Bearing Nude Mice PHY906 was previously found to potentiate the antitumor activity of capecitabine in human HepG2 xenografts. An experiment was therefore conducted to study whether PHY906 could enhance the antitumor activity of capecitabine in human Panc-1 xenografts. Total 20 NCr nude mice transplanted with Panc-1 human pancreatic carcinoma cells were divided into 4 groups (N=5 mice/group): Group (A) vehicle control; Group (B) treated with PHY906 (500 mg/kg, bid, day 1-4, 8-11, 15-18, 22-25 and 29-32); Group (C) treated with capecitabine (720 mg/kg, bid, day 1-7, 15-21, and 29-32); and Group (D) treated with PHY906 (500 mg/kg, bid, days day 1-4, 8-11, 15-18, 22-25 and 29-32) plus capecitabine (720 mg/kg, bid, day 1-7, 15-21, and 29-32). PHY906 was found to enhance the antitumor activity of capecitabine, as shown in FIG. 6. A similar observation was found with lower doses of capecitabine (data not shown).

All applications, patent, and publications referenced herein are incorporated by reference to the same extent as if each individual application, patent, and publication was specifically and individually indicated to be incorporated by reference. Specifically, the disclosures of WO 01/66123. WO 06/053049, U.S. Pat. No. 7,025,993, US 2005/0196473, and US 2003/0211180 are incorporated herein by reference in their entirety for all purposes. Furthermore, the following references and their contents are herein incorporated by reference in their entirety for all purposes:

1. Bergsland, E. K. and Venook, A. P. Hepatocellular Carcinoma [Gastrointestinal Tract]. Current Opinion in Oncology, 12: 357-361, 2000.
2. Fernandez-Zapico, M. E., Kaczynski, J. A., and Urrutia, R. Pancreatic Cancer Research: Challenges, Opportunities, and Recent Developments. Curr Opin Gastroenterol, 18: 563-567, 2002.
3. Jemal, A., Thomas, A., Murray, T., and Thun, M. Cancer Statistics, 2002. CA Cancer J Clin, 52: 23-47, 2002.
4. Skolnick, A. A. Basic Science Focus of Third International Symposium on Liver Cancer and Hepatitis. The Journal of the American Medical Association, 276: 1457-1458, 1996.
5. Abbruzzese, J. L. New Applications of Gemcitabine and Future Directions in the Management of Pancreatic Cancer. Cancer Supplement, 95: 941-945, 2002,
6. Hertel, L. W., Boder, G. B., Kroin, J. S., Rinzci, S. M., Poore. G. A., Todd, G. C., and Grindey, G. B. Evaluation of the Antitumor Activity of Gemcitabine (2',2'-Difluoro-2'-deoxycytidine). Cancer Res., 50: 4417-4422, 1990.
7. Pettersson, F., Colston. K. W., and Daigleish, A. G. Retinoic Acid Enhances the Cytotoxic Effects of Gemcitabine and Cisplatin in Pancreatic Adenocarcinoma Cells. Pancreas, 23: 273-279, 2001.
8. Philip, P. A. Gemcitabine and PLatinum Combinations in Pancreatic Cancer. Cancer Supplement, 95: 908-911, 2002.
9. Schultz, R. M., Meriiman, R. L., Toth, J. E., Zimmermann, J. E., Hertel, L. W., Andis, S. L., Dudley, D. E., Rutherford. P. G., Tanzer, L. R., and Grindey, G. B. Evaluation of New Anticancer Agents against the MIA paCa-2 and PANC-1 Human Pancreatic Carcinoma Xenografts. Oncology Research, 5: 223-228, 1993.
10. Von Hoff, D. D. and Bearss, D. New drugs for patients with pancreatic cancer. Current Opinion in Oncology, 14: 621-627, 2002.
11. Brims, C. J., Harbison, M. T., Davis, D. W., Portera, C. A., Tsan, R., McConkey, D. J., Evans, D. B., Abbruzzese, J. L., Hicklin, D. J., and Radinsky, R. Epidermal Growth Factor Receptor Blockade with C225 Plus Gemcitabine Results in Regression of Human Pancreatic Carcinoma Growing Orthotopically in Nude Mice by Antiangiogenic Mechanisms. Clinical Cancer Research, 6: 1936-1948, 2000.
12. Jacobs, A. D. Gemcitabine-Based Therapy in Pancreas Cancer: Gemcitabine-Docetaxel and Other Novel Combinations. Cancer Supplement, 95: 923-927, 2002.
13. McGinn, C. J., Lawrence, T. S., and Zalupski, M. M. On the Development of Gemcitabine-Based Chemoradiotherapy Regimens in Pancreatic Cancer. Cancer Supplement, 95: 933-940, 2002.
14. Oettle, H. and Riess, H. Gemcitabine in Combination with 5-Fluorouracil with or without Folinic Acid in the Treatment of Pancreatic Cancer. Cancer Supplement, 95: 912-922, 2002.
15. Gelmon, K., Chan, A., and Harbeck, N. The role of capecitabine in first-line treatment for patients with metastatic breast cancer. The Oncologist. 11(suppl 1): 42-51, 2006.
16. Ershler, W. B. Capecitabine monotherapy: safe and effective treatment for metastatic breast cancer. The Oncologist. 11(4):325-35, 2006.
17. Martin, M. J. Current stage-specific chemotherapeutic options in colon cancer. Expert Rev Anticancer Ther. 5(4):695-704, 2005.
18. Cartwright. T. H., Cohn, A., Varkey, J. A., et al. A Phase II study of oral capecitabine in patients with advanced or metastatic pancreatic cancer. J Clin Oncol. 20: 160-164, 2002.
19. Lozano, R. D., Patt, V. Z., Hassan, M. M., Frome, A., Vauthey, J. N., Ellis, L. M., Schnirer, T. D., Brown, J. L., Abbruzzese. J. L., Wolff, R. A., and Charnsangavej, C. Oral Capecitabine (Xeloda) for the treatment of hepatobiliary cancers (hepatocellular carcinoma, cholangiocarcinoma, and gallbladder cancer). Proc Am Soc Clin Oncol. 19:1025A, 2000
20. Strumberg, D., Richly, H., Hilger, R. A., et al. Phase I clinical and phannacokinetic study of the novel Raf kinase and vascular endothelial growth factor receptor inhibitor BAY 43-9006 in patients with advanced refractory solid tumors. J Clin Oncol. 23: 965-972, 2005
21. Abou-Alfa, G. K., Schwartz, L., Ricci, S., et al. Phase II study of sorafenib in patients with advanced hepatocellular carcinoma. J Clin Oncol. 24:4293-4300
22. ACS Cancer Facts and Figures. American Cancer Society, 2004.
23. Raymond, E., Faivre, S., Chancy, S., Woynarowski, J., and Cvitkovic, E. Cellular and Molecular Pharmacology of Oxaliplatin. Molecular Cancer Therapeutics, 1: 227-235, 2002.
24. Diggle. P. J., Liang, K. Y., and Zeger, S. L. Analysis of Longitudinal Data, 2nd cd. Oxford: Oxford Science Publications, 1994.

We claim:

1. A method of treating cancer in a mammal in need comprising administering to said mammal an anticancer composition in one or two parts comprising a therapeutically effective amount of sorafenib and an herbal preparation consisting essentially of a combination of *Scutellaria baicalensis, Glycyrrhiza uralensis, Ziziphus jujuba* and *Paeonia lactiflora*, wherein said composition is formulated in pharmaceutical dosage form in combination with a pharmaceutically acceptable carrier, additive and/or excipient thereof.

2. The method according to claim 1 wherein said composition is in oral dosage form.

3. The method according to claim 1 wherein said composition is administered in two parts.

4. The method according to claim 2 wherein said composition is administered in two parts.

5. The method according to claim 1 wherein said cancer is a gastrointestinal cancer.

6. The method according to claim 2 wherein said cancer is a gastrointestinal cancer.

7. The composition according to claim 1 wherein said cancer is hepatocellular cancer, colorectal cancer or pancreatic cancer.

8. The method according to claim 1 wherein said cancer is hepatocellular cancer, colorectal cancer or pancreatic cancer.

9. The method according to claim 1 wherein said cancer is hepatocellular cancer.

10. The method according to claim 2 wherein said cancer is hepatocellular cancer.

11. The method according to claim 1 wherein said cancer is colorectal cancer.

12. The method according to claim 2 wherein said cancer is colorectal cancer.

13. The method according to claim 1 wherein said cancer is pancreatic cancer.

14. The method according to claim 2 wherein said cancer is pancreatic cancer.

15. The method according to claim 1 wherein said mammal is a human patient.

16. The method according to claim 2 wherein said mammal is a human patient.

17. The method according to claim 3 wherein said mammal is a human patient.

18. The method according to claim 4 wherein said mammal is a human patient.

19. The method according to claim 5 wherein said mammal is a human patient.

20. The method according to claim 7 wherein said mammal is a human patient.

\* \* \* \* \*